(12) United States Patent
Frost

(10) Patent No.: US 10,884,032 B1
(45) Date of Patent: Jan. 5, 2021

(54) REMOTE DETECTION OF ELECTRICAL ACTIVITY IN A TARGET VOLUME

(71) Applicant: Holloway H. Frost, Houston, TX (US)

(72) Inventor: Holloway H. Frost, Houston, TX (US)

( * ) Notice: Subject to any disclaimer, the term of this patent is extended or adjusted under 35 U.S.C. 154(b) by 295 days.

(21) Appl. No.: 16/156,522

(22) Filed: Oct. 10, 2018

Related U.S. Application Data

(60) Provisional application No. 62/570,528, filed on Oct. 10, 2017.

(51) Int. Cl.

| | | |
|---|---|---|
| *G01R 31/00* | (2006.01) | |
| *G01R 15/26* | (2006.01) | |
| *A61B 5/00* | (2006.01) | |
| *A61B 5/05* | (2006.01) | |
| *G01R 15/24* | (2006.01) | |
| *G01R 19/00* | (2006.01) | |
| *G01R 33/032* | (2006.01) | |

(52) U.S. Cl.
CPC ............... *G01R 15/26* (2013.01); *A61B 5/05* (2013.01); *A61B 5/7203* (2013.01); *G01R 15/241* (2013.01); *G01R 15/246* (2013.01); *G01R 15/247* (2013.01); *G01R 19/0092* (2013.01); *G01R 31/001* (2013.01); *G01R 33/0322* (2013.01); *G01R 15/24* (2013.01); *G01R 15/242* (2013.01); *G01R 15/245* (2013.01)

(58) Field of Classification Search
CPC ................ G01R 15/246; G01R 15/241; G01R 19/0092; G01R 15/247; G01R 33/0322; G01R 15/24; G01R 15/242; G01R 15/245
USPC ................................ 324/72, 76.11–76.83, 96
See application file for complete search history.

(56) References Cited

U.S. PATENT DOCUMENTS

| | | | | |
|---|---|---|---|---|
| 2010/0240999 A1* | 9/2010 | Droitcour | ............ | A61B 5/7203 600/453 |
| 2010/0249630 A1* | 9/2010 | Droitcour | ............. | A61B 5/1113 600/529 |
| 2010/0249633 A1* | 9/2010 | Droitcour | ............... | G01S 13/88 600/534 |

\* cited by examiner

*Primary Examiner* — Raul J Rios Russo
(74) *Attorney, Agent, or Firm* — Rao DeBoer Osterrieder, PLLC; Dileep P. Rao

(57) ABSTRACT

A non-invasive method of detecting electrical activity in a target volume. The method can comprise aiming a plurality of antennas at one or more target sub-volumes within a target volume and acquiring the radio signal created when an electrical discharge occurs. The method can then comprise processing the radio signals to determine the electrical activity within the target volume and displaying the electrical activity in the target volume.

6 Claims, 1 Drawing Sheet

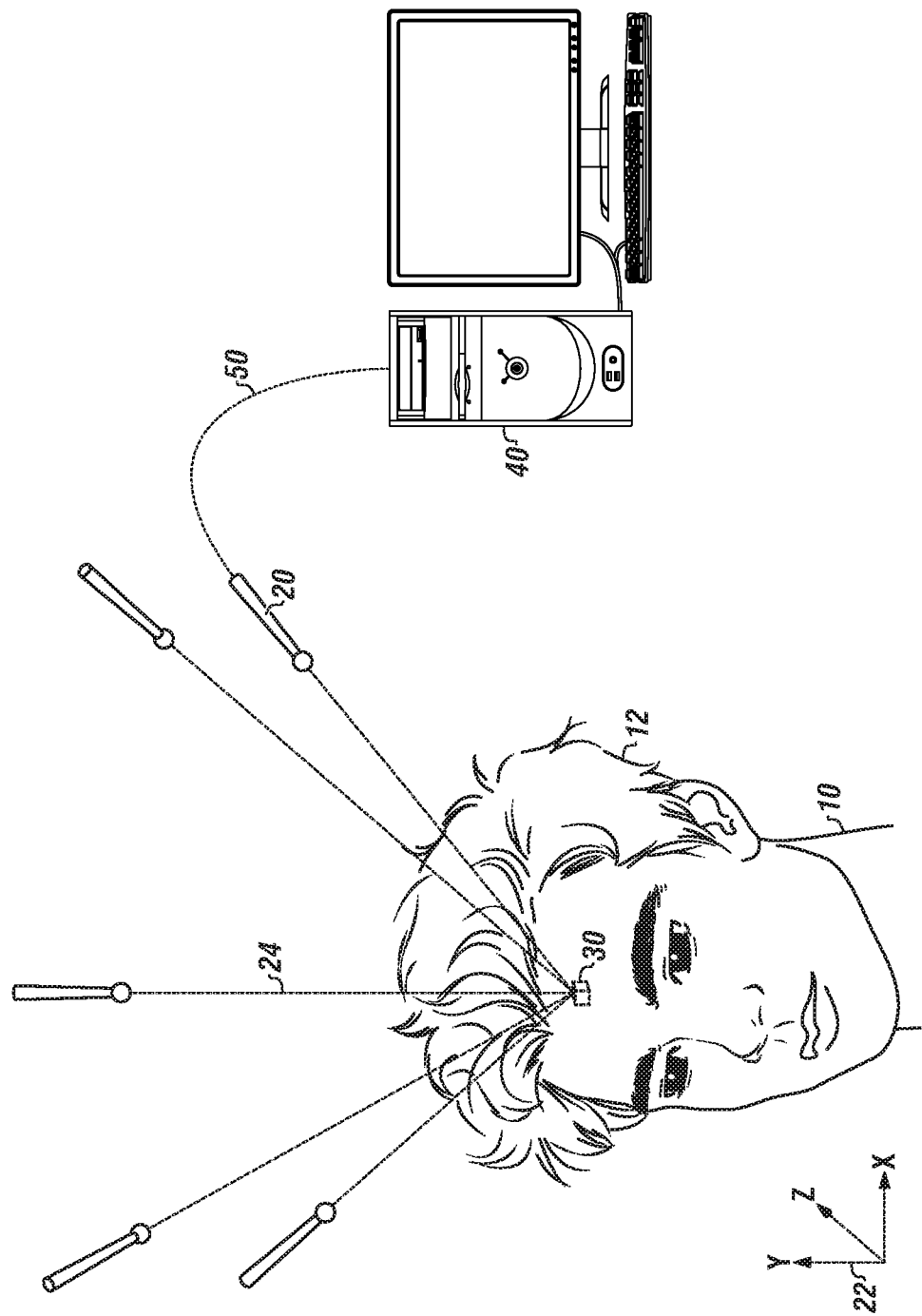

REMOTE DETECTION OF ELECTRICAL ACTIVITY IN A TARGET VOLUME

CROSS REFERENCE TO RELATED APPLICATION

The current application claims priority to and the benefit of U.S. Provisional Patent Application Ser. No. 62/570,528 filed on Oct. 10, 2017, titled "REMOTE DETECTION OF ELECTRICAL ACTIVITY IN A TARGET VOLUME". This reference is hereby incorporated in its entirety herein.

FIELD

The present disclosure generally relates to methods and apparatus for the remote detection of electrical activity within a target volume.

BACKGROUND

Often there is localized electrical activity in a given volumetric space. It is desirable to have an understanding of actual and relative quantitative measures of such activities. Invasive measurement techniques are often not feasible due to various constraints, such as affecting the readings themselves, inability to place probes or sensors, difficult to access target volumes, shifting or fluctuating target volumes, and the like.

A typical example of such a situation is the study of physiological processes such as the human brain and/or human muscles. Especially for physiological applications, it is desirable to establish a non-invasive measurement technique and/or apparatus.

Various other topics can lend themselves to application of the present methods and apparatus. Possible applications can include the testing and/or study of printed circuit boards, detection of land mines or other electronic equipment, the study of geological phenomena, such as ball lightning, and the like.

Especially for physiological phenomena, present methods such as EEG, MRI, fMRI, PET, NIRS, fNIRS, etc. have various shortcomings. They are either indirect measures (PET, NIRS, fNIRS), have lower than desired resolution (EEG), have too great a time lapse for a wholistic picture (MRI, fMRI), or simply cost too much for widespread implementation. Further, these techniques often require costly equipment and are somewhat inconvenient for the subject being tested.

A need exists, therefore to have a non-invasive, high resolution, rapid, and cost-effective method and apparatus for measuring or imaging specific and/or relative electrical activity in a target volume, such as a brain, a muscle or muscle group, a geological location, and the like.

The present disclosure meets these needs.

BRIEF DESCRIPTION OF THE DRAWING

The detailed description will be better understood in conjunction with the accompanying drawing as follows:

FIGURE is an example embodiment of the present disclosure for the purpose of neural imaging is shown.

The present embodiments are detailed below with reference to the listed FIGURE.

DETAILED DESCRIPTION OF THE EMBODIMENTS

Before explaining the present disclosure in detail, it is to be understood that the disclosure is not limited to the specifics of particular embodiments as described and that it can be practiced, constructed, or carried out in various ways.

While embodiments of the disclosure have been shown and/or described, modifications thereof can be made by one skilled in the art without departing from the spirit and teachings of the disclosure. The embodiments described herein are exemplary only, and are not intended to be limiting.

Specific structural and functional details disclosed herein are not to be interpreted as limiting, but merely as a basis of the claims and as a representative basis for teaching persons having ordinary skill in the art to variously employ the present invention. Many variations and modifications of embodiments disclosed herein are possible and are within the scope of the present disclosure.

Where numerical ranges or limitations are expressly stated, such express ranges or limitations should be understood to include iterative ranges or limitations of like magnitude falling within the expressly stated ranges or limitations.

The use of the word "a" or "an" when used in conjunction with the term "comprising" in the claims and/or the specification may mean "one," but it is also consistent with the meaning of "one or more," "at least one," and "one or more than one."

The use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, and the like.

Accordingly, the scope of protection is not limited by the description herein, but is only limited by the claims which follow, encompassing all equivalents of the subject matter of the claims. Each and every claim is hereby incorporated into the specification as an embodiment of the present disclosure. Thus, the claims are a further description and are an addition to the embodiments of the present disclosure.

The inclusion or discussion of a reference is not an admission that it is prior art to the present disclosure, especially any reference that may have a publication date after the priority date of this application. The disclosures of all patents, patent applications, and publications cited herein are hereby incorporated by reference, to the extent they provide background knowledge; or exemplary, procedural or other details supplementary to those set forth herein.

The embodiments of the present disclosure generally relate to methods and apparatus for the non-invasive detection and measurement of electrical activity within a target volume and presenting an image of such electrical activity.

The methods and apparatus make use of the principle that electrical currents generate radio waves and that there is a distinct relationship between radio wave creation and electrical current flow. The flow of electrical current establishes a related magnetic field. When the field is established, a radio wave is emitted. When electrical flow stops, the magnetic field collapses, also emitting a radio wave.

Any change in flowing electrical current, such as the discharge of a battery or the firing of a synapse in the human body will therefore generate a radio wave. Utilizing this principle, the presence of radio waves can establish the presence of electrical activity.

By using directional or high gain antennas to receive radio waves and processing the received signals, a remote measurement of electrical activity becomes possible. Depending on the application, and desired information, relative comparisons within the target volume can be made, or actual electrical current values can be calculated/determined.

In embodiments, the methods can involve the steps of: identifying a target volume, providing a plurality of antennas distributed three dimensionally, subdividing the target volume into one or more discrete sub-volumes, aiming each antenna at a target sub-volume within the target volume, acquiring a radio signal from each target sub-volume, and processing the radio signal to determine electrical activity in each target sub-volume, displaying the electrical activity within the target volume.

The identification of a target volume entails determining a region of interest for which it is desirable to know the electrical activity within. For example, studies of the brain may identify a patient's head as the target volume. Other physiological target volumes may be specific muscles or muscle groups. In embodiments, the target volume may be any region of space or a specific piece of machinery.

The target volume can be of virtually any size and shape, with the limitation being application specific, such as the number of antennas available for use, the required resolution, the amount of time available for sampling, computing power, and the like.

Persons having ordinary skill in the art will recognize that the size, shape, data requirements, and overall complexity of the target volume will determine apparatus needs.

Once a target volume is identified, a plurality of antennas can be provided. It is preferable to utilize directional (or high gain) antennas to allow for aiming and/or "focusing" of the antennas to receive signals from a specific direction, such as along the axis of the antenna.

Further, determining the relative positions of the antennas and their direction of aim can allow for persons having ordinary skill in the art to determine an intersection of the antennas' focus within the target volume. Antennas which are spatially distributed can be aimed or focused at a single target volume, thereby providing signal data from a plurality of antennas regarding a specific target volume.

Antennas can be of suitable characteristics based upon the signal being received. Various radio frequencies can be "listened" for by the antenna.

When detecting physiological activity, antennas may need to be sensitive at low frequencies, such as from below 1 Hz to 30 Hz. In other applications, antennas may need to be sensitive to much higher frequencies, such as in the gigahertz, terahertz, or even higher ranges. The present disclosure is intended to cover any radio frequency without limitation. Persons having ordinary skill in the art can make the appropriate antenna selection based upon specific application requirements.

The antennas can be distributed three dimensionally in a spatial array around the target volume. The antennas can all be aimed or focused within the target volume. In embodiments, the antennas can be repositioned to cover various regions of the target volume. The antennas' positions relative to each other, as well as relative to the target volume can be known. With known positioning of each antenna, the intersection of the focus or aim of a plurality of antennas within the target volume can be determined.

In embodiments, the target volume can be divided in to discrete target sub-volumes within the target volume. Persons having ordinary skill in the art can select the number of discrete sub-volumes, and a size of the sub-volume. In embodiments, the sub-volume can be the entire target volume.

Each antenna can be aimed at a target sub-volume. In embodiments, one or more antennas can be aimed at one or more sub-volumes. Based upon frequency of electrical activity within the target volume, sampling volumes and sampling times can be modified by persons having ordinary skill in the art. In embodiments, at least two antennas can be aimed at each sub-volume within the target volume.

In specific applications, each antenna can be aimed at a different sub-volume, thereby simultaneously encompassing the entire target volume. Typically, such applications would be for target volumes known to emit high frequency, powerful radio waves that are easily received by the used antenna. In embodiments, at least two antennas can be aimed at each sub-volume, thereby providing a redundant reading from each sub-volume.

In other applications, with low frequency or low power radio waves a single sub-volume, or a group of sub-volumes can be sampled for a specified time frame, and antennas can be repositioned to sample other sub-volumes. Preferably, each sub-volume of a target volume can be sampled by at least one antenna.

It can be especially beneficial to have multiple antennas trained upon a sub-volume for the purpose of aiding in the elimination or reduction of electrical and/or signal noise during processing. In applications where the signals are of very low intensity or power, all available antennas can be trained upon a sub-volume. When all antennas are trained upon the same sub-volume, multiple readings from various directions can be combined and processed to determine electrical activity in the sub-volume.

The signal received by each antenna can be amplified and transmitted to a computer for data storage and analysis. The computer can be any device with a processor (microprocessor) and a data storage comprising a non-transitory data storage medium.

The computer can further have instructions instructing the processor to: process a signal or signals received from one or more antennas, cancel noise from the received signal(s), and graphically or numerically display electrical activity in the target volume.

Radio signals can be processed by any means known to persons having ordinary skill in the art. In embodiments, all antennas can be sequentially trained upon various target sub-volumes within the target volume until the desired target volume has been completely encompassed. Upon processing of the signals, the target volume has been imaged for electrical activity, and data can be displayed graphically, numerically, as a three-dimensional projection, and the like. In other embodiments, antennas can be trained upon groups of sub-volumes to define a plane or a volumetric region of interest within the target volume.

For example, if a brain is being imaged for electrical activity utilizing a currently disclosed method, the antennas can be trained upon cross sections of the brain sequentially until the entire brain is covered. Alternatively, various lobes of the brain can be targeted as volumetric regions of interest by the antennas for imaging. Also, the brain can be imaged during activities of particular interest, such as during exercise, seizures, etc.

An apparatus for implementing the steps of the methods can be provided. The apparatus can comprise a plurality of antennas, an optional amplifier, and a computer.

The antennas of the apparatus can be spatially distributed in a three-dimensional array allowing for the antennas to be pointed at a target volume. While the simplest geometric arrangement would be a spherical arrangement of antennas, no specific arrangement is required. The antennas can be placed in any geometric arrangement wherein their positions relative to one another and their positions relative to the target volume are known.

The antennas can be high gain or directional antennas as the application warrants. The antennas can be actuated either manually, or via automated mechanical means. Any actuators known to persons having ordinary skill in the art can be utilized to position the antennas as desired. In embodiments, a computer can control the positioning and aiming of the antennas.

The antennas can be positioned in such a manner that their direction of focus intersects the target volume at a desired target sub-volume. The antennas can be positioned such that all target sub-volumes are intersected simultaneously.

In embodiments, the antennas can be positioned to intersect a single target sub-volume or a group of target sub-volumes and then sequentially repositioned to intersect other target sub-volumes or groups of target sub-volumes.

The antennas can optionally be in electronic communication with an amplifier to amplify radio signals received from within the target volume.

The antennas can be in electronic communication with a computer, either directly or through the amplifier if used. The computer can be configured to store data received from the antennas and process the received signals to determine electrical activity within the target volume.

The computer can further be configured to display the electrical activity in the target volume numerically, graphically, as a three-dimensional projection, or any other method for displaying data.

Using known signal processing and noise cancellation methods, persons having ordinary skill in the art can be utilized to process/combine received data and determine electrical activity in a target volume.

As the typical antenna will be directional and can intersect with multiple other antennas at various target sub-volumes, the processing of the signals involves a significant degree of complexity and the mechanics of such processing is outside the scope of this disclosure. However, the multifaceted and comprehensive radio signal data received can provide a detailed and extremely high-resolution representation of electrical activity.

Turning now to the FIGURE, an embodiment of the present disclosure for the purpose of neural imaging is shown.

Shown in the FIGURE is a subject 10 and the subject's head is shown as the target volume 12. A plurality of antennas 20 can be trained on the target volume 12. The antennas can have a known location, such as a known relative distance 24 from the target volume 12 along the x, y, and z axes 22 from the target volume 12.

The target volume 12 can be further subdivided into target sub-volumes 30. Radio signals 50 acquired by the antenna 20 can be sent to a computer 40 for storage of data and signal processing.

While the present disclosure emphasizes the embodiments, it should be understood that within the scope of the appended claims, the disclosure might be practiced other than as specifically described herein.

What is claimed is:

1. A method of detecting electrical activity in a target volume comprising:
   a. identifying a target volume;
   b. providing a plurality of antennas distributed three dimensionally;
   c. aiming each antenna of the plurality of antennas at the target volume;
   d. acquiring a radio signal from the target volume; and
   e. processing the radio signal to determine electrical activity in the target volume.

2. The method of claim 1, further comprising:
   a. subdividing the target volume into one or more discrete sub-volumes;
   b. aiming each antenna of the plurality of antennas at a target sub-volume within the target volume;
   c. acquiring a radio signal from each target sub-volume; and
   d. processing the radio signal to determine electrical activity in each target sub-volume.

3. The method of claim 1, further comprising storing radio signal data on a non-transitory data storage medium.

4. The method of claim 1, further comprising displaying the electrical activity within the target volume.

5. The method of claim 1, further comprising a computer instructing a processor to process the radio signal or radio signals received from one or more antennas, cancel noise from the received signal(s), and graphically or numerically display the electrical activity in the target volume.

6. The method of claim 2, further comprising displaying the electrical activity within each target volume.

* * * * *